(12) United States Patent
Ramanjaneyulu et al.

(10) Patent No.: US 7,468,442 B2
(45) Date of Patent: Dec. 23, 2008

(54) PROCESS FOR THE PREPARATION OF CARVEDILOL FORM-II

(75) Inventors: Gorantla Seeta Ramanjaneyulu, Secunderabad (IN); Indukuri Venkata Sunil Kumar, Hyderabad (IN); Ketavarapu Narasimha Rao, Hyderabad (IN); Jammula Vera Venkata Krishna Kishore, Hyderabad (IN)

(73) Assignee: Matrix Laboratories Ltd., Andhra Pradesh (IN)

( * ) Notice: Subject to any disclaimer, the term of this patent is extended or adjusted under 35 U.S.C. 154(b) by 492 days.

(21) Appl. No.: 10/552,843

(22) PCT Filed: Apr. 16, 2004

(86) PCT No.: PCT/IN2004/000104

§ 371 (c)(1),
(2), (4) Date: Oct. 12, 2005

(87) PCT Pub. No.: WO2004/094378

PCT Pub. Date: Nov. 4, 2004

(65) Prior Publication Data

US 2007/0055069 A1    Mar. 8, 2007

(30) Foreign Application Priority Data

Apr. 21, 2003  (IN) .................. 328/MSA/2003

(51) Int. Cl.
C07D 209/82  (2006.01)

(52) U.S. Cl. .............. 548/444; 548/416; 548/427; 548/439; 548/440

(58) Field of Classification Search ........ 548/416, 548/427, 440, 444
See application file for complete search history.

(56) References Cited

U.S. PATENT DOCUMENTS

| 4,503,067 | A | 3/1985 | Wiedemann et al. |
| 4,697,022 | A | 9/1987 | Leinert |
| 4,985,454 | A | 1/1991 | Leinert |
| 6,403,579 | B1 * | 6/2002 | Heller .............. 514/223.5 |
| 6,710,184 | B2 * | 3/2004 | Kor et al. ............ 548/444 |
| 6,730,326 | B2 * | 5/2004 | Beyer et al. .......... 424/489 |

FOREIGN PATENT DOCUMENTS

| EP | 0918055 A1 | 5/1999 |
| WO | WO 99/05105 A1 | 2/1999 |
| WO | WO 01/87837 A1 | 11/2001 |
| WO | WO 02/00216 A1 | 1/2002 |

* cited by examiner

Primary Examiner—Golam M Shameem
(74) Attorney, Agent, or Firm—Schweitzer Cornman Gross & Bondell LLP

(57) ABSTRACT

The present invention provides a cost-effective, industrially feasible process for the manufacture of crystalline Carvedilol Form-II using novel Carvedilol salts comprising a step of reacting 4-(2,3-epoxy propoxy)carbazole (II) with 2-(2-methoxy phenoxy)ethyl amine (III) followed by acidification with mineral acid in presence of an organic solvent to yield acid addition salts, treatment of the said salts with base(s) in presence of organic solvent(s), water and isolation from the organic solvent(s) followed by crystallization from ethyl acetate.

9 Claims, 4 Drawing Sheets

PROCESS FOR THE PREPARATION OF CARVEDILOL FORM-II

Figure 1:
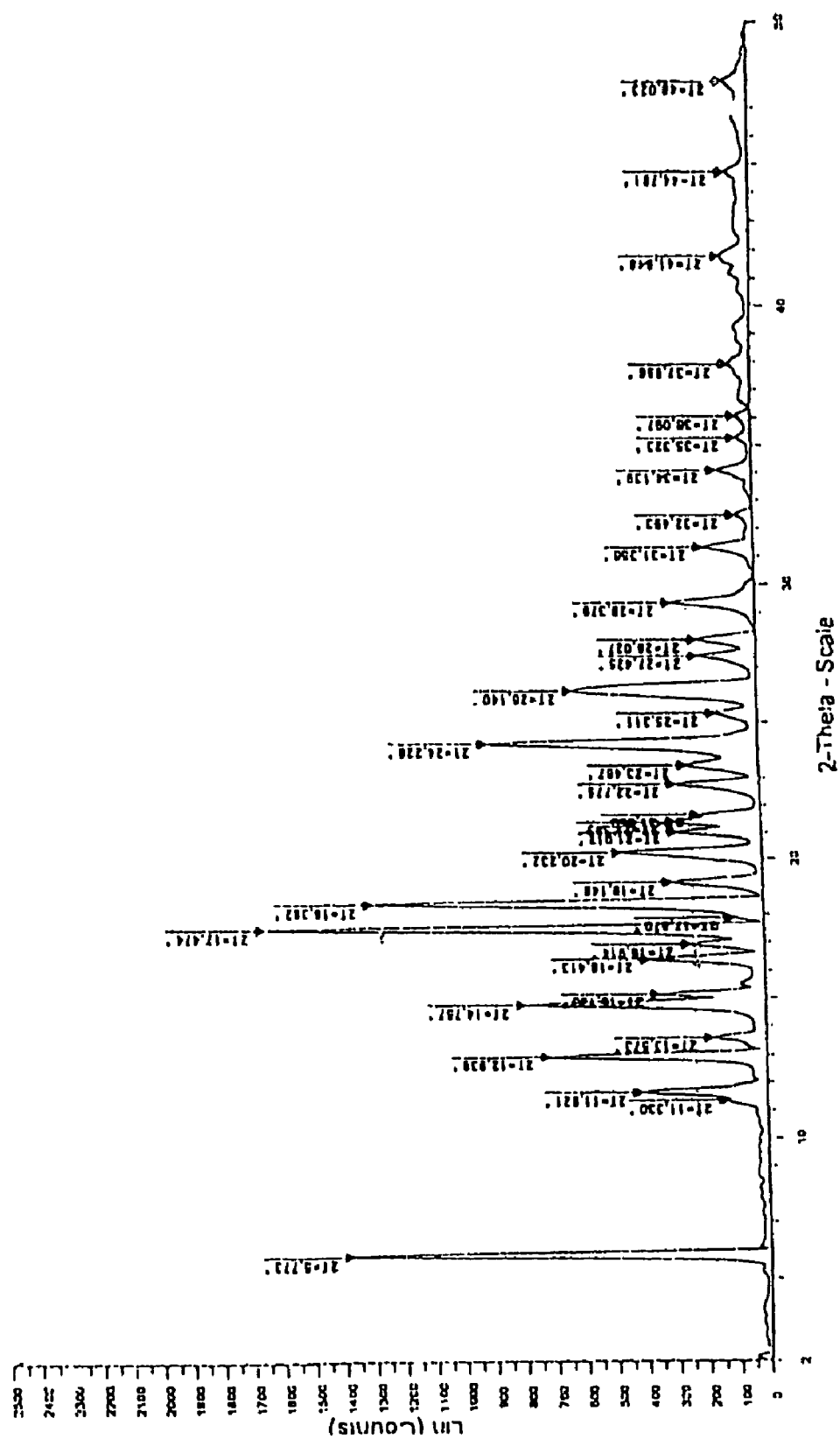

The present invention relates to a new process involving minimal workup steps without using strong mineral acids and avoiding any degradation of the final product for the preparation of Carvedilol Form-II using novel Carvedilol salts.

Carvedilol is a non-selective β-adrenergic blocking agent with vasodilating activity. Carvedilol, (±) 1-(9H-carbazol-4-yloxy)-3[[2-(2-methoxy phenoxy)ethyl]amino]-2-propanol [CAS Registry No 7295609-3] has the structure of Formula-1

Formula-1

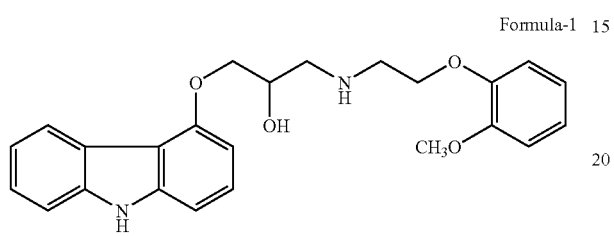

Carvedilol has a chiral center and can exist either as individual stereo isomer or in racemic form. Racemic Carvedilol is the active ingredient of COREG®, which is indicated for the treatment of congestive heart failure and hypertension. Both the racemate and stereoisomers may be obtained accordingly to procedures well known in the art (EP 0 127 099).

Various routes of synthesis have been used or suggested for the preparation of Carvedilol. Thus EP 0 004 920 reported the preparation of Carvedilol by reaction of 4-(2,3-epoxy propoxy)carbazole (II) with 2-(2-methoxy phenoxy)ethyl amine (III).

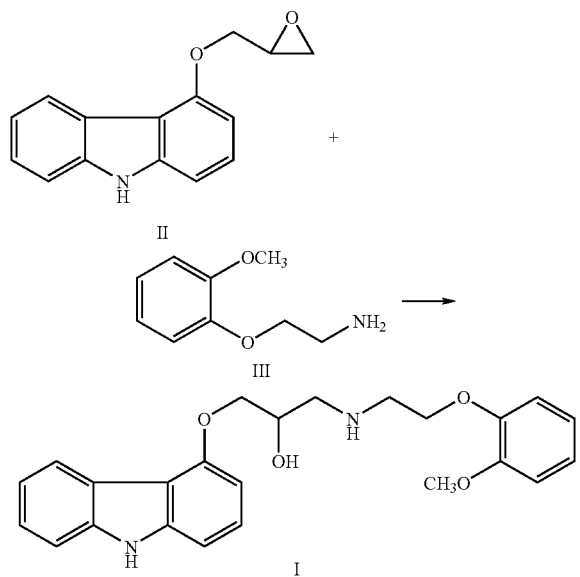

The above process produces a low yield of Carvedilol at least in part because in addition to Carvedilol, the process leads to the production of a bis impurity (IV) of the following structure

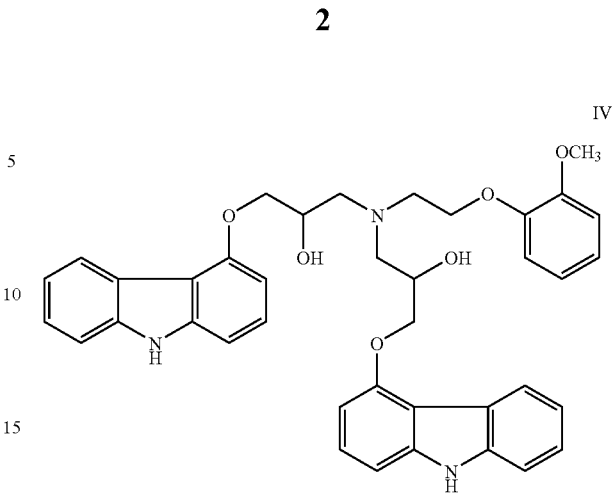

EP 0 918 055 discloses that the Formation of the bis compound (IV) can be avoided by protecting the 'N' atom in 2-(2-methoxy phenoxy)ethylamine before reaction with 4-(2,3-epoxy propoxy)carbazole using a benzyl group as a protection group. The product benzyl-Carvedilol (V) Formed has to be debenzylated before the desired product Carvedilol is formed, where debenzylation is done by hydrogenative debenzylation. This procedure clearly introduces two additional steps in the synthesis, namely a benzylation and a debenzylation step.

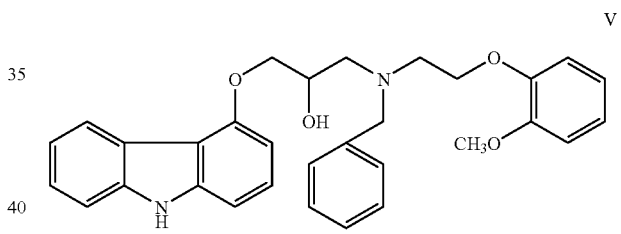

PCT Publication WO 01/87837 describes the synthesis of Carvedilol by the reaction of 4-hydroxy carbazole with 5-chloromethyl-3-(2-(2-methoxy phenoxy)ethyl)-oxazolidin-2-one (VI). The 5-(9H-carbazol-4-yloxy methyl)-3-[2-(2-methoxy phenoxy)ethyl]oxazolidin-2-one (VII) Formed has to be hydrolyzed before the desired product Carvedilol is formed.

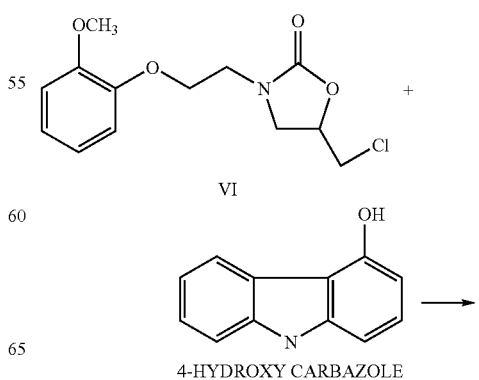

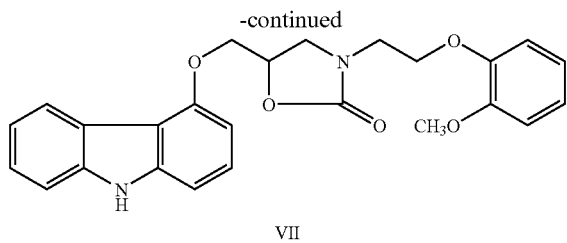

VII

Moreover the preparation of 5-chloromethyl-3-[2-(2-methoxy phenoxy)ethyl]-oxazolidin-2-one (VI) requires sequence of reactions viz-reaction of 1,3-dichloro propan-2-ol with phenyl chloroformate followed by condensation of the resulting intermediate 2-methoxy phenoxy ethylamine thereby introducing a number additional steps in the synthesis. The publication also discloses hydrolysis of VII to Carvedilol in acidic medium and formation of salts.

PCT Publication WO 02/00216 describes the preparation of Carvedilol by reaction of 4-(2,3-epoxy propoxy)carbazole (II) with 2-(2-methoxy phenoxy)ethyl amine (III) in which the formation of bis compound (IV) can be avoided by taking large molar excess of III, the reaction being carried out in absence of solvent or in presence of solvents toluene, xylene and heptane. In the same publication the process for isolation of Carvedilol as crystalline hydrochloride is described to obtain the crystalline hydrochloride, hydrochloride hydrate and methyl ethyl ketone-solvate. The crude Carvedilol was isolated as hydrochloride salt after an elaborate work-up using strong acid like hydrochloric acid at pH 3.0-5.0. The use of large molar excess of 2-(2-methoxy phenoxy)ethyl amine (III) (2.8 mol-6.0 mol for 1.0 mol of 4-(2,3-epoxy propoxy) carbazole (II) makes this process uneconomical. Moreover the use of strong mineral acids for the salt Formation can lead to decomposition of the product.

It has been a long standing need in industry to provide a process for the preparation of Carvedilol involving minimal workup steps without using strong mineral acids and avoiding any degradation of the final product.

The present invention provides a cost-effective, industrially feasible process for the manufacture of crystalline Carvedilol Form-II using novel Carvedilol salts such as oxalate, salicylate, comprising a step of reacting 4-(2,3-epoxy propoxy)carbazole (II) with 2-(2-methoxy phenoxy)ethyl amine (III) in molar ratio of about 1:2 to about 1:2.5, followed by acidification with mineral acid in presence of an organic solvent to yield acid addition salts, treatment of the said salts with base(s) in presence of organic solvent(s), water and isolation from the organic solvent(s) followed by crystallization from ethyl acetate.

FIG. 1: X-ray diffraction pattern of the Carvedilol Form-II (Prepared as per the examples)

Figure 2:
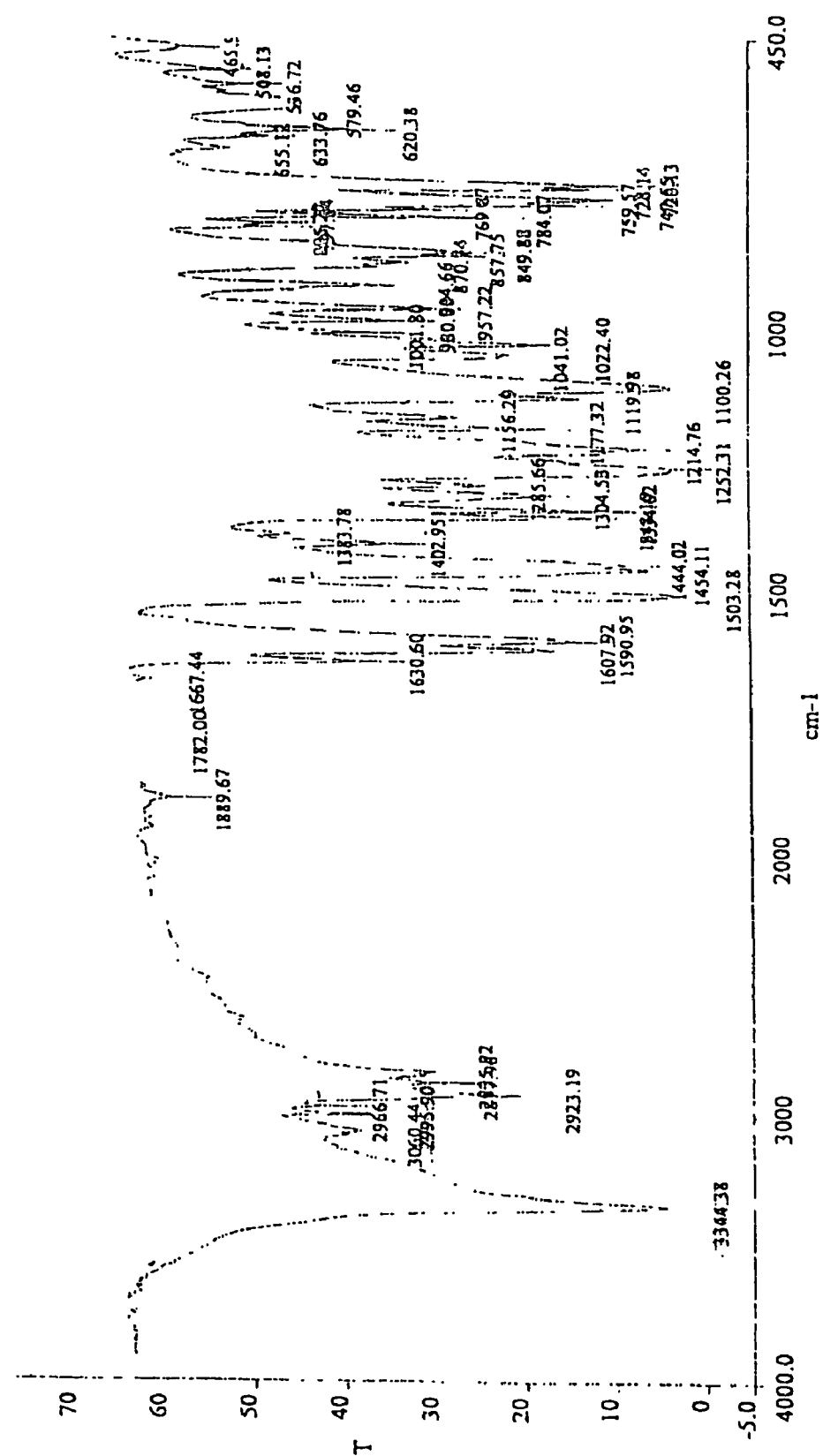

FIG. 2: FTIR spectrum of the Carvedilol Form-II (Prepared as per the examples)

Figure 3:
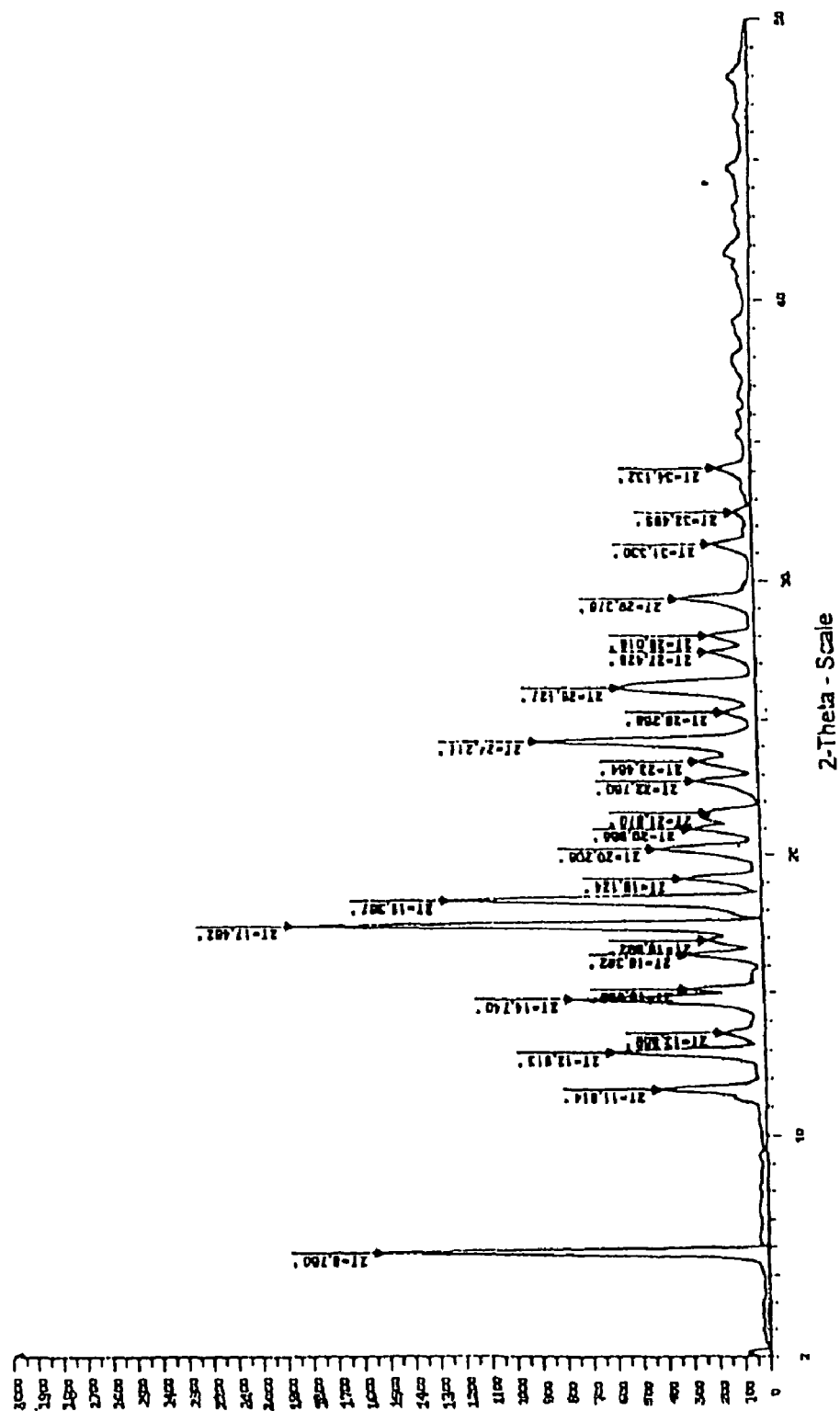

FIG. 3: X-ray diffraction pattern of the Carvedilol Form-II

Figure 4:
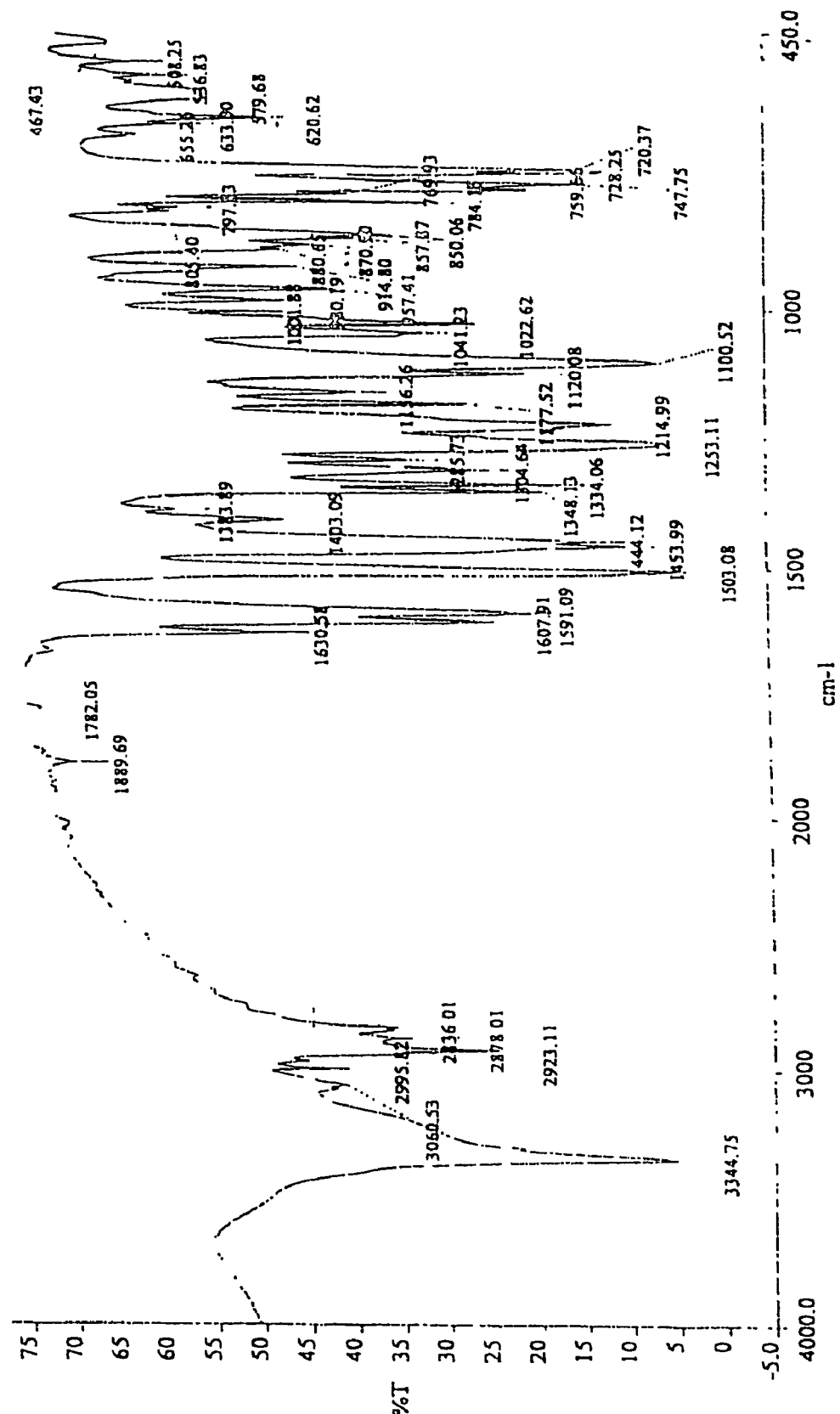

FIG. 4: FTIR spectrum of the Carvedilol Form-II

The essential features of the present invention is the process for the manufacture of Carvedilol Form-II using novel salts of Carvedilol which comprises of the steps:

1. Reaction of 4-(2,3-epoxy propoxy)carbazole with 2-(2-methoxy phenoxy)ethyl amine in the molar ratio of 1:2.0-1:2.5 in presence of solvent(s)
2. Adjustment of pH after the completion of reaction with organic acid(s) in presence of water, organic solvent(s) and isolation of the Carvedilol salts
3. Treatment of the salts with base(s) in a biphasic system of water and an water immiscible organic solvent(s)
4. Separation of the water immiscible organic solvent(s), isolation and crystallization of the Carvedilol from ethyl acetate Both the crude Carvedilol and recrystallized Carvedilol obtained by the process of the present, invention are in the polymorphic Form-II and are anhydrous, as is evident from the IR spectrum and X-Ray diffraction pattern.

The required 4-(2,3-epoxy propoxy)carbazole is prepared by the reaction of 4-hydroxy carbazole with epichlorohydrin in presence of potassium iodide and potassium carbonate in acetone at reflux temperature followed by removal of inorganics, distillation of the solvent and crystallization of the residue with methanol.

The reaction of 4-(2,3-epoxy propoxy)carbazole with 2-(2methoxy phenoxy ethylamine is carried out in presence of solvent at reflux temperature. The preferred molar ratio of 4-(2,3-epoxy propoxy)carbazole and 2-(2-methoxy phenoxy)ethylamine is 1:20 to about 1:2.5.

The solvents preferred are chlorobenzene, monoglyme (ethylene glycol diethyl ether), the reaction temperature is in the range of about 125° C. to about 140° C., preferably about 130° C. to about 133° C. with chlorobenzene as solvent and in the range of about 80° C. to about 90° C., preferably 87° C. to about 90° C. with monoglyme as solvent.

The work-up of reaction mass for isolation of salts varies based on the solvent medium. When the reaction medium is monoglyme, after the completion of reaction, the solvent is distilled off followed by addition of water and organic solvent(s), adjusting the pH of the reaction mass to about 2.0 to about 3.0 with organic acid(s) at temperature of about 40° C. and cooling the reaction mass to about 20° C. to about 25° C. The organic solvent is selected from isopropyl acetate or monochlorobenzene. When the reaction medium is chlorobenzene after completion of reaction, water is added and the pH is adjusted with organic acid(s) at above 40° C. temperatures. The preferred organic acid is oxalic acid, salicylic acid or mixtures thereof and preferred temperature is about 45° C. to about 50° C. and the pH is about 2.5 to about 2.8. The precipitated Carvedilol salts (Carvedilol oxalate, Carvedilol salicylate) is isolated by filtration, centrifugation etc.

The Carvedilol salt is suspended in water, followed by addition of methylene chloride and basified to pH of about 9.0 to about 9.5 with suitable base(s) such as alkali, alkaline metal hydroxides, ammonia, organic bases such as triethyl amine, methyl amine at 20° C. to about 25° C. and stirred for about 1 hr to about 2 hrs. The preferred base is thy ammonia solution. The reaction mass is allowed to settle and the layers are separated. The organic layer is dried over dehydrating agents such as anhydrous sodium sulphate, magnesium sulphate. The solvent is distilled off from the dried organic layer. The residue obtained is crystallized from ethyl acetate by dissolving in hot condition and then cooling to 0° C.-10° C. The Carvedilol so obtained may be further recrystallized from ethyl acetate to obtain a pharmaceutically acceptable quality.

The invention is now illustrated with non-limiting examples

EXAMPLE-1

Step-1: Preparation of (2,3-Epoxy propoxy)carbazole 100 g (0.55 moles) of 4-hydroxy carbazole is dissolved in 600 ml of acetone. To that 188 g (1.36 moles) potassium carbonate, 2.0 g potassium iodide and 0.5 g sodium dithionate are added under nitrogen. The reaction mass is refluxed for 1.0 hr, cooled to room temperature followed by the addition of 150 g (1.62 moles) of epichlorohydrin through a dropping funnel over 40-45 min at room temp. The reaction mass is further refluxed for 32 hrs and then cooled to room temp and filtered. The above filtrate is evaporated followed by recrystallisation of the crude product from methanol.

Yield: 92 g (69.9% yield).
M.P: 121° C.-126° C.
Purity: Above 98%

Step-2: Preparation of 1-(9H-carbazol-4-yloxy)-3[[2-(2-methoxy phenoxy)ethyl]amino]-2-propanol oxalate (Carvedilol oxalate)

174 g (1.04 moles, 2.5 mol equivalents) of 2-(2-methoxy phenoxy)ethylamine is dissolved in 500 ml of monochlorobenzene. The temperature is raised to 125° C. under stirring. 100 g (0.42 moles) of 4-(2,3-epoxy propoxy)carbazole is slowly added in five lots during 1 hr at reflux temperature. Refluxing is then carried on for two hrs. The reaction is monitored to completion by thin layer chromatography and then cooled to 90° C. 500 ml water is then charged followed by cooling to 70° C. The pH of reaction mass is adjusted to 2.5-2.7 with 10% oxalic acid solution at 60° C.-70° C. Stirring is done for one hr at 60° C.-70° C. The reaction mass is cooled to room temp and maintained for two hrs. The material is filtered and washed with water and dried at 50° C.-60° C.

Yield: 160 g (77% yield)
M.P: 186° C.-188° C.
(C, 63.01; H, 5.72; N, 5.68; Calculated for $C_{26}H_{28}N_2O_8$ C, 62.90; H, 5.68; N, 5.64; IR Analysis: $cm^{-1}$ 3447, 3056, 1607, 1456, 1264, 1216, 1187, and 1024: 1H NMR (300 MHz, DMSO-d6) δ 11.25(1H,s, COOH), 8.2(1H,d, Ar—H), 7.44 (1H,d, Ar—H), 7.30(2H,m, Ar—H), 7.10-7.15(2H,d, Ar—H), 6.80-7.05(4H,m, Ar—H), 6.66(1H,d,Ar—H), 4.25 (2H,d,$OCH_2$), 4.15(2H,t,$OCH_2$), 3.70(3H,s, $OCH_3$), 3.13 (2H,t, $CH_2$), 3.11 (1H,m, CH), 3.05(2H,d,$CH_2$): $^{13}C$ NMR (75 MHz, DMSO-$d_6$) δ 66.5, 154.8, 149.4, 147.6, 141.3, 139, 126.4, 124.5, 122.7, 121.7, 120.7, 18.7, 14.5, 112.3, 111.6, 110.5, 104.2, 70.2, 66.5, 66.4, 55.4, 51.4, and 47.1)

Step-3: Preparation of 1-(9H-carbazol-4-yloxy)-3[[2-(2-methoxy phenoxy)ethyl]amino]-2-propanol (Carvedilol)

160 g of the oxalate salt is dissolved in 1500 ml methylene chloride and to that 600 ml of water is charged. The pH is adjusted to pH 9.0-9.3 with aq ammonia. The reaction mass is stirred for one hr at room temp and the organic layer is separated. The aqueous layer is again extracted with 750 ml of methylene chloride. The total methylene chloride layers are combined and dry over sodium sulphate followed by distillation of the methylene chloride. 700 ml of ethyl acetate is charged and the system is refluxed for 15 minutes and then is slowly cooled to 10° C. and maintained at this temperature for two hrs. The material is filtered and washed with chilled ethyl acetate following by drying at 50° C.-60° C. The resulting material was recrystallized in ethyl acetate.

Yield: 88 g (76% yield)
M.P: 114° C.-116° C.
Purity: Above 99.5%

EXAMPLE-2

Step-2: Preparation of 1-(9H-carbazol-4-yloxy)-3[[2-(2-methoxy phenoxy)ethyl]amino]-2-propanol oxalate (Carvedilol oxalate)

146.4 g (0.875 moles, 2.1 mol equivalents) of 2-(2-methoxy phenoxy)ethylamine is dissolved in 500 ml of monochlorobenzene and the temperature is raised 125° C. under stirring. 100 g (0.42 moles) of 4-(2,3-epoxy propoxy)carbazole is slowly added in lots over 1 hr at reflux temperature. Reflux is then carried on for two hrs. Distilled of the monochlorobenzene under vacuum followed by cooling of the reaction mass to 50-60° C. 1000 ml isopropyl acetate is charged followed by the addition of 1000 ml DM water. pH of reaction mass is adjusted to 2.0-2.5 with 10% oxalic acid solution at 45° C.-50° C. Stirred for one hr at 45° C.-50° C., the reaction mass is cooled to room temperature and maintained for two hrs. The material is filtered washed with isopropyl acetate and water mixture and then dried at 50° C.-60° C.

Yield: 155 g (74.6% yield)
M.P: 184° C.-188° C.
(C, 63.01; H, 5.72; N, 5.68; Calculated for $C_{26}H_{28}N_2O_8$ C, 62.90; H, 5.68; N, 5.64.

IR Analysis: $cm^{-1}$ 3447, 3056, 1607, 1456, 1264, 1216, 1187, and 1024: $^1H$ NMR (300 MHz, DMSO-d6) δ 11.25(1H, s, COOH), 8.2(1H,d, Ar—H), 7.44(1H,d, Ar—H), 7.30(2H, m, Ar—H), 7.10-7.15(2H,d, Ar—H), 6.80-7.05(4H,m, Ar—H), 6.66(1H,d,Ar—H),4.25(2H,d,$OCH_2$), 4.15(2H,t, $OCH_2$), 3.70(3H,s, $OCH_3$), 3.13 (2H,t, $CH_2$), 3.11(1H,m, CH), 3.05(2H,d,$CH_2$): $^{13}C$ NMR (75 MHz, DMSO-d6) δ 66.5, 154.8, 149.4, 147.6, 141.3, 139, 126.4, 124.5, 122.7, 121.7, 120.7, 18.7, 14.5, 112.3, 111.6, 110.5, 104.2, 70.2, 66.5, 66.4, 55.4, 51.4, and 47.1)

Step-3: Preparation of 1-(9H-carbazol-4-yloxy)-3[[2-(2-methoxy phenoxy)ethyl]amino]-2-propanol (Carvedilol)

This can be performed as described in Step-3 of Example-1
Yield: 88 g (63.2%)
M.P: 114° C.-116° C.

EXAMPLE-3

Similarly was prepared the Carvedilol salicylate which is converted to Carvedilol in overall yield of 59% from 2-(2-methoxy phenoxy)ethylamine
Analysis of carvedilol Salicylate:
(C, 68.4; H, 6.03; N, 5.44: Calculated for $C_{31}H_{32}N_2O_7$ C, 68.37; H, 5.92, N, 5.14:IR Analysis: $cm^{-1}$ 3424, 2932, 1457, 1385, 1256, 1223, 1179, 1107, 1027, 754, and 721)

The present invention provides a novel, commercially feasible process to obtain Carvedilol Form-II of pharmaceutically acceptable quality using novel salts of Carvedilol without involving elaborative work-up. Further the present invention avoids the use of strong mineral acids thereby eliminating any possibility of decomposition of the product.

The invention claimed is:
1. A process for the preparation of crystalline Carvedilol Form-II using novel salts of Carvedilol, comprising the steps of:
   reacting 4-(2,3-epoxy propoxy) carbazole with 2-(2-methoxy phenoxy) ethyl amine in the molar ratio of 1:2.0 to 1:2.5 in an organic solvent selected from monochlorobenzene, ethylene glycol dimethyl ether (monoglyme) and mixtures thereof, adjusting the pH after completion of the reaction with at least one organic acid in the presence of water and at least one organic solvent and isolating the produced novel Carvedilol salts, treating the Carvedilol salts with at least one base in the presence of water and methylene chloride followed by separation of organic aqueous layers, and drying the organic layer followed by removal of the at least one organic solvent and crystallization of the residue in ethyl acetate.

2. A process as claimed in claim 1, wherein the at least one organic acid is selected from oxalic acid and salicylic acid.

3. A process as claimed in claim 1, wherein the pH is adjusted to 2.0 to about 3.0.

4. A process as claimed in claim 1, wherein the at least one organic solvent used during pH adjustment is selected from isopropyl acetate, chlorobenzene and mixtures thereof.

5. A process as claimed in claim 1, wherein the at least one base is selected from alkali, alkaline metal hydroxides, ammonia, and organic bases.

6. A process as claimed in claim 1 wherein the at least one base is aq. ammonia.

7. A process as claimed in claim 1, wherein the novel Carvedilol salts are carvedilol oxalate and carvedilol salicylate.

8. A process as claimed in claim 3, wherein the pH is adjusted to 2.5 to about 2.8.

9. A process as claimed in claim 5 wherein the at least one base is aq. ammonia.

* * * * *